United States Patent [19]
Petrie, III et al.

[11] Patent Number: 5,853,986
[45] Date of Patent: Dec. 29, 1998

[54] CHEMICAL PROMOTION OF NUCLEIC ACID HYBRIDIZATION

[75] Inventors: Charles Robert Petrie, III, Woodinville, Wash.; Lisa Marie Rutledge, Brea, Calif.; Jerold Randall Morgan, Renton, Wash.

[73] Assignee: Becton Dickinson and Company, Franklin Lakes, N.J.

[21] Appl. No.: 490,036

[22] Filed: Jun. 13, 1995

Related U.S. Application Data

[63] Continuation of Ser. No. 140,694, Oct. 21, 1993, abandoned, which is a continuation of Ser. No. 503,441, Apr. 2, 1990, abandoned.

[51] Int. Cl.$^6$ .................................................. C12Q 1/68
[52] U.S. Cl. ............................................................ 435/6
[58] Field of Search ................................................ 435/6

[56] References Cited

U.S. PATENT DOCUMENTS

| | | | |
|---|---|---|---|
| 4,302,204 | 11/1981 | Wahl et al. | |
| 4,689,294 | 8/1987 | Boguslawski et al. | 435/6 |
| 4,925,785 | 5/1990 | Wang et al. | 435/6 |
| 5,512,436 | 4/1996 | Stone | 435/6 |

FOREIGN PATENT DOCUMENTS

WO 89/05357  6/1989  WIPO.

OTHER PUBLICATIONS

Wetmur, J.G., "Acceleration of DNA Renaturation Rates," *Biopolymers* 14:2517–2524 (1975).

Singer, R.H., et al., "Optimization of In Situ Hybridization Using Isotopic and Non–Isotopic Detection Methods," *BioTechniques* 4:230–250 (1986).

Meinkoth, J. and J. Wahl, "Hybridization of Nucleic Acids Immobilized on Solid Supports," *Anal. Biochem.* 138:267–284 (1984).

Beckmann, A.M., et al., "Detection and Localization of Human Papillomavirus DNA in Human Genital Condylomas by In Situ Hybridization with Biotinylated Probes," *J. Med. Virol.* 16:265–273 (1985).

Milde, K. and T. Loning, "Detection of Papillomavirus DNA in Oral Papillomas and Carcinomas: Application of In Situ Hybridization with Biotinylated HPV 16 Probes," *J. Oral. Pathol.* 15:292–296 (1986).

McDougall, J.K. et al., "Methods for Diagnosing Papillomavirus Infection," in *Papillomaviruses*, Wiley, Chicester (CIBA Foundation Symposium 120), pp. 86–103 (1986).

Amasino, R.M., "Accelaration of Nucleic Acid Hybridization Rate by Polyethylene Glycol," *Anal. Biochem.* 152:304–307 (1986).

Syvanen, A., et al., "Fast Quantification of Nucleic Acid Hybrids by Affinity–based Hybrid Collection," *Nucleic Acids Res.* 14:5037–5048 (1986).

*Primary Examiner*—Scott W. Houtteman
*Attorney, Agent, or Firm*—David W. Highet, Esq.

[57] ABSTRACT

An improved method is described for increasing the rate and specificity of hybridization of target polynucleotide sequences with complementary probes. The method uses amphipathic hydrocarbon polymers (AHP), exemplified by polyvinyl sulfonic acid or polystyrene sulfonic acid, to effect the improved hybridization characteristics. The method may be used in solution phase, solid phase, or in situ hybridization formats.

8 Claims, No Drawings

CHEMICAL PROMOTION OF NUCLEIC ACID HYBRIDIZATION

This is a continuation of application Ser. No. 08/140,694, filed Oct. 21, 1993, now abandoned, which was a continuation of Ser. No. 07/503,441, filed Apr. 2, 1990, now abandoned.

Field of the Invention

The present invention relates to methods generally useful in the field of recombinant nucleic acid technology and related fields. More particularly, this invention relates to the use of amphipathic polymers for accelerating the rate of hybridization between complementary strands of nucleic acids, and for lowering non-specific background binding.

BACKGROUND OF THE INVENTION

Other workers have attempted to enhance hybridization rates by the use of chemical agents in conjunction with the probe polynucleotide. U.S. Pat. No. 4,302,204, issued to Wahl, et al., discusses the use of "volume exclusion agents" to increase in situ hybridization rates. Use of such "volume exclusion agents" as dextran sulfate and other charged polysaccharides to enhance solid phase hybridization kinetics have been described. Also, Wetmur (1975) *Biopolymers,* 14:2517 reports that 10% dextran sulfate accelerates DNA hybridization by 10-fold. Dextran sulfate is a commonly used "volume exclusion agent." In situ hybridization is particularly problematic due to the inability of the probes to readily enter into the nucleus or cytoplasm in which their target sequences are located. To solve problems associated with in situ hybridization, researchers have attempted to reduce the size of the probes and to alter cell fixation procedures to facilitate entry of the probes into the cytoplasm or nucleus. See generally, WO 89/05357; Singer, R. H., et al., "Optimization of In Situ Hybridization Using Isotopic and Non-Isotopic Detection Methods," *Biotechniques* 4(3):230–250 (1986). Meinkoth J. and Wahl J., "Hybridization of Nucleic Acids Immobilized on Solid Supports" (Review), *Anal. Biochem.,* 138:267–284 (1984) generally describes solid phase hybridization.

The in situ localization of human papillomavirus (HPV) DNA using long biotinylated probes in the presence of dextran sulfate has been reported. Beckmann, P. M., et al., "Detection and Localization of Human Papillomavirus DNA in Human Genital Condylomas by In Situ Hybridization with Biotinylated Probes," *J. Med. Virol.,* 16:265–273 (1985); Milde K., Loning, T., "Detection of Papillomavirus DNA in Oral Papillomas and Carcinomas: Application of In Situ Hybridization with Biotinylated HPV 16 probes," *J. Oral. Path.,* 15:292–296 (1986); and McDougall, J. K., et al., "Methods for Diagnosing Papillomavirus Infection," in *Papillomaviruses,* Wiley, Chicester (CIBA Foundation Symposium 120), pp. 86–103 (1986).

U.S. Pat. No. 4,689,294 issued to Boguslawski, et al., discloses the use of anionic polyacrylate salts and polymethacrylate salts to enhance the rate of hybridization between complementary polynucleotide segments.

Amasino, R. M., "Acceleration of Nucleic Acid Rate by Polyethylene Glycol," *Anal. Biochem.,* 152:304–307 (1986) and Syvanen, A. C. et al., "Fast Quantification of Nucleic Acid Hybrids by Affinity-based Hybrid Collection," *Nucleic Acids Res.,* 14(12):5037–5048 (1986) have reported that polyethylene glycols can be used to enhance the rate of hybridization of soluble oligonucleotides to oligonucleotides bound to a solid support.

In the field of medical and clinical diagnosis using nucleic acid hybridization, the need for rapid assay tests for the accurate and reproducible detection of nucleic acids has been a longstanding problem. Classical hybridization assays driven to completion would often require incubation times of as long as 24–36 hours or more, depending upon the concentrations of the complementary strands and other conditions. They would also typically be plagued by low signal-to-noise ratios. Thus, there is a need for an improved procedure for use, particularly in a clinical diagnostic context, that provides means to accelerate these typically multi-hour long incubations and to decrease the nonspecific background levels, yet does not adversely affect the specificity of the hybridizations. The present invention fulfills these and other needs.

SUMMARY OF THE INVENTION

The present invention discloses the use of particular classes of hydrocarbon polymers to increase the rate of hybridization of complementary polynucleotides. The rate enhancement is observed in nucleic acid hybridization assays, including solution phase, solid phase and in situ hybridizations. Moreover, this class of compounds effects improved binding specificities between probe and target sequences resulting in lowered background.

This invention specifically provides for methods of conducting a nucleic acid hybridization assay in a hybridization medium containing complementary nucleic acid sequences, said method comprising: (a) adding an amphipathic hydrocarbon polymer (AHP), said polymer comprising acidic moieties having a dissociation constant of less than about 4.0, to the hybridization medium; and (b) detecting the presence of hybridized nucleic acid. In particular the invention provides for the AHP to be added in an amount effective to result in an increased rate of hybridization for the complementary nucleic acid and in an amount sufficient to reduce non-specific background where nucleic acids are binding non-specifically to each other, to any solid supports used in the assays, or to the cellular matrix of an in situ assay. It is preferred that the addition of AHP is in an amount to accelerate the hybridization rate at least 20% above a control assay having no AHP added but all other aspects of the assay being identical. It is also preferred that the addition of AHP is in an amount to reduce non-specific binding of nucleic acid to at least about 15% of the resulting background of a control assay having no AHP added but all other aspects of the assay being identical. The phrase "in an amount sufficient" refers to an amount of AHP that will provide a detectable result when compared to control assays.

The molecular weight of the AHP described above are preferably in excess of about 10,000 daltons and most preferably above about 50,000 daltons. The dissociation constant ($pK_a$) of the AHP is preferably less than about 3.5. The preferred amounts of AHP (by weight) present in the hybridization medium is at least 1.0%, more preferably at least 5.0% and most preferably 10% of the total weight of the hybridization medium. The preferred AHP polymers are polyvinyl sulfonic acid (PVSA), polystyrene sulfonic acid (PSSA) or polyanethole sulfate (sodium salt).

The acidic moieties are preferably selected from the group consisting of: phosphates ($-OPO_3^{2-}-OP(OR_1)O_2-$), sulfates ($-OSO_3^-$), sulfonates ($-SO_3^{31}$) and phosphonates ($-PO_3^{2-}$, $-P(OR_1)O_2^-$) wherein $R_1$ is an organic radical.

The preferred assay formats are heterogeneous hybridization assays and in situ hybridization assays.

There are also provided herein methods of conducting a hybridization between complementary nucleic acid strands comprising the step of including in a hybridization mixture an anionic hydrocarbon polymer (AHP) comprising subunits having a formula:

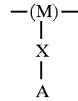

wherein M is a polymerized monomer; X, is either a covalent bond directly linking A with M or is a multi-atom spacer group; and A is an acidic moiety with a dissociation constant ($pK_a$) of less than about 4.0. It is preferred that the acidic moieties, A, are selected from the group described above with the further proviso that A is not a carboxyl group (—COOH). H is preferably a divalent radical derived from monovalent radicals selected from the group consisting of: phenyl, benzyl (benzoylene), naphthyl, alkyl, alkenyl, alkynyl, acrylyl or acyl groups. The preferred amounts of polymer and the choices of polymer are as previously described.

There is also described herein kits for conducting the above described assays. These kits typically include compartments, at least one compartment containing an amphipathic hydrocarbon polymer for addition to a hybridization medium where complementary binding between a nucleic acid probe and said sample occurs. Additional compartments would comprise nucleic acid probes, positive controls of nucleic acid sequences similar to the target samples being assayed for and signal oligonucleotides for detection of hybridization.

One preferred disclosed polymer is polystyrene sulfonic acid (PSSA). PSSA shows dramatic advantages over dextran sulfate, giving a greater increase in hybridization rate while decreasing nonspecific nucleic acid binding.

DETAILED DESCRIPTION OF THE INVENTION

The invention relates to methods for conducting a nucleic acid hybridization assay in a hybridization medium containing complementary nucleic acid sequences which comprises adding an amphipathic hydrocarbon polymer (AHP) to the hybridization medium, in an amount sufficient to accelerate the rate of hybridization between the complementary nucleic acid sequences, to lower non-specific background hybridization, or to achieve both, and detecting the presence of hybridized nucleic acid. The polymers may be any of a wide variety of hydrocarbon polymers, which contain appropriate amphipathic subunits in a proportion suitable to effectuate the desired results of accelerated hybridization and reduced non-specific background.

The AHPs comprise substantial proportions of amphipathic subunits potentially interspersed with other subunits. An amphipathic subunit has both hydrophobic and strongly acidic hydrophilic properties, typically resulting in natural partition of such molecules at interfaces between hydrophobic and hydrophilic phases. The subunits are repeated forming a macromolecule having a hydrophobic backbone with sidechains containing hydrophilic groups. The hydrophilic portion comprises an anionic group with a dissociation constant ($pK_a$) of the acid form of the anionic group preferably less than about 4.0. Generally, a less basic anionic group is preferred. While not wishing to be limited by theory, it is presently hypothesized that those polymers bearing the stronger acid groups are better able to substitute for nucleic acids at non-specific binding sites than the volume exclusion agents currently being employed.

The AHPs will typically comprise substantial proportions of subunits with the following generalized formula:

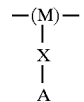

where
M is a backbone component or monomer;
X is either a covalent bond directly linking A with M, or is a spacer moiety; and
A is an acidic moiety.

The AHPs will typically have a backbone component (M) comprising polymerized subunits, preferably unsaturated organic compound, and will typically have at least one chemically activatable moiety such as a carboxyl, alkene, alkyne, hydroxyl, thiol, or amine that is reactive with other subunits to form the polymer backbone. The polymerization reaction will typically proceed via a condensation reaction, as in the case of polypeptides and polyamides, by free-radical initiated reactions, as with polyacrylates and polyacrylamides, or thermally, as in the case of polyethylene. Other mechanisms for polymerization may also be utilized. See, for example, Chapter 32 of Morrison and Boyd, *Organic Chemistry*, 3rd ed., Allyn and Bacon, which is incorporated herein by reference. The AHP backbone may comprise linear monomers, ringed monomers, branched monomers or a combination of these monomers which are linked together into a polymer. Typical AHP backbones, often substituted, include polyvinyl, polyacrylate, polyamido, polyacrylamido, polyacrylo, polyester or polypeptide chains.

A monomer refers to a subunit but does not imply that the monomer necessarily be polymerizable with the spacer and anionic groups in the final forms present in the AHP. Often the backbone will be formed first, and the spacer and anion groups will be added by substitution or modification of the backbone.

The hydrocarbon polymer backbone will preferably be linear, but may contain branched structures. Polymers with backbones in the range of 2,000 to 100,000 daltons are preferred. Polymers may be primarily homopolymers, and these homopolymers might be linked together by identical (e.g., head to tail), nonidentical (e.g., head to head and tail to tail) or mixed combinations of types of linkages. Alternatively, the polymers may comprise heterogeneous subunits, or be composed of combinations of various different types of subunits (e.g., copolymers), in an ordered or random sequence. It is not necessary for the polymer to be made of 100% amphipathic subunits. The polymer will function acceptably with less than 100% amphipathic subunits. Heterogeneous polymers with 20–50%, 50–80% and up to 100% amphipathic subunits will function. The minimum percentage of amphipathic subunits that will create a polymer capable of competing with nucleic acid for non-specific bind sites will vary with the hybridization assay conditions. Routine titration experiments will permit one to determine optimum conditions for each polymer.

The chemical linker arm or spacer group (X) of the AHP may provide particular electronic and/or steric advantages related to the hypothesized interaction between the "volume exclusion agent" and a hybridizing polynucleotide. The spacer group is a noncritical element of the AHP. Typical spacers include a covalent bond or a divalent radical derived from the group of monovalent radicals consisting of saturated or unsaturated alkyls of 1 to 10 carbons, (an alkylidene bridge, e.g., —CH—(CH$_2$)$_n$—CH or an acrylyl—CH:CHO—) aryls of 6 to 10 carbons, cycloalkyls of 5–14 carbons, acyl groups (—R$_2$—C:O—), of 2 to 12 carbons inclusive of the acyl carbons, heterocycles and heteroaromatics. R$_2$ may be optionally substituted. Examples include methylene, ethylene and other alkyl groups, phenyl or substituted phenyl groups, e.g., 1,2 (ortho), 1,3 (meta) or 1,4 (para) substitutions, benzyl groups, naphthyl, or heteroaromatic groups. The spacers will typically be hydrocarbon moieties and can be linear, branched or ringed structures. The spacers are non-critical elements of the AHP and will typically be of a molecular weight of between 14 and 500.

The divalent radicals of X are typically positioned so that the points of juncture between M and A are at maximum length. For example, naphthylene, phenylene, benzoylene and methylene bridges are derived from naphthyl, phenyl, benzyl and alkyl radicals. However, ortho and meta attachments are not excluded.

By substituted, it is meant that 1–3 radicals are bound to the spacer. These radicals may be identical or different and include: halo, nitro, amine, lower alkyl or lower alkoxy groups. Hetero refers to stable hydrocarbon rings comprising 4–12 members where at least one and up to three members may be oxygen, nitrogen or sulfur atoms. "Lower" alkyl or alkoxy groups comprise 1 to 4 carbons. Unless otherwise stated, all ranges of carbons are inclusive.

The acidic groups (A) on the AHPs will generally be weakly anionic. Typical weakly anionic groups include phosphates (—OPO$_3^{2-}$, —OP(OR$_1$)O$_2^-$), sulfates (—OSO$_3^-$), sulfonates (—SO$_3^-$) or phosphonates (—PO$_3^{2-}$, —P(OR$_1$)O$_2^-$). Where the acidic moiety is substituted by R$_1$, the substituent R$_1$ may be any organic radical which preserves the required dissociation constant. For example, this noncritical substituent may be the same or different than the monovalent radicals from which divalent spacer groups (X) are derived. More particularly R$_1$ may be alkyl, cycloalkyl, heterocyclic, aryl or aralkyl where each is a stable member having at least one carbon for the alkyls and up to fourteen carbons for larger members or having about 15 to 250 atomic mass units. Lower alkyls of 1–4 carbons are preferred. The acidic groups may also be substituted alkyl carboxylates where the pKa of the carboxy group is less than 4.0. Examples include halogen-substituted carboxylates such as dichloro- or difluoro- acetates.

The acidic moieties may also comprise substituted phenolic compounds such as 1-hydroxy, 2,4-dinitrophenyl or 1-hydroxy, 2,4,6-trinitrophenyl.

The AHPs of this invention are conveniently made by methods well known to those skilled in the art of polymer chemistry. Many AHPs are available commercially from various venders. For those AHPs not commercially available, well-known techniques of preparation are employed to manufacture them. Generally, monomeric subunits having formula M—X—A, and combinations thereof, are polymerized "as is,"n in their unprotected forms. This method of making the polymers is particularly suitable when the X and A moieties remain chemically "inert," i.e., do not participate, in the polymerization step which forms the polymer backbone. Backbone formation will be initiated in a manner corresponding to the type of polymerization reaction employed, e.g., a free radical initiator is used to initiate formation of a polymer chain that propagates by free-radical polymerization.

Occasionally, one or more subunits having formula M—X—A will be "protected" during the polymerization step. For example, when A is a carboxylic acid group, A may be protected by an alkyl or aryl group during the polymerization step, then deprotected, e.g., by hydrolysis, after the polymer backbone is formed. A useful treatise disclosing methods of making AHPs is Seymour & Carrahar, *Polymer Chemistry, An Introduction*, Marcel Dekker, Inc. 1987, which is incorporated herein by reference.

The AHPs will typically be used at concentrations ranging from about 1% to about 20%. Their sizes will range from about 10,000 to about 500,000 daltons. Typically, these hydrocarbon polymers will be added into the buffer solution containing the probe polynucleotides, but they may also be present in solution with target sequences.

Suitable hydrocarbon polymers include polyvinyl sulfonic acid (PVSA), polystyrene sulfonic acid (PSSA), and polyanethole sulfonate (sodium salt), which are preferred embodiments. PVSA and PSSA are commercially available from Aldrich Chemical Co., Milwaukee, Wis. USA and polyanethole sulfonate is commercially available from Sigma Chemical Co.; St. Louis, Mo. Polymers having an approximate molecular weight of between 10,000 to 500,000 daltons can be used in concentrations of between about 1–20%. These anionic polymers are available in various salt forms, e.g., sodium, potassium or ammonium. The salt form is typically a non-critical aspect of the invention. The cation is selected so as to be compatible with the other components of the hybridization medium.

The hybridization medium will typically contain various constituents in addition to the AHPs including, but not limited to, buffers, detergents, organic solvents, surfactant proteins and non-specific nucleic acids.

The AHPs will typically be included in concentrations sufficient, when used for hybridization acceleration purposes, to accelerate the rate of hybridization by at least about 20%, more usually by at least about 40% and preferably by at least about 60%. When used for background lowering purposes, the AHPs will be added in amounts sufficient to lower the non-specific background by at least about 15%, usually at least about 25% and preferably by at least about 35%. Typically, a combination of the two effects will be desired, and AHPs will be included at concentrations sufficient to provide an acceptable combination of acceleration and background lowering.

In one preferred embodiment, the AHP is PSSA used at a concentration in the hybridization medium normally between about 1% and 20%, preferably about 5% for solid phase hybridizations and about 12% for in situ hybridizations. The molecular weight is normally between about 10,000 daltons and about 500,000 daltons, preferably about 126,000 daltons. Correspondingly comparable molecular lengths for other AHP molecules are preferred.

Traditional and accepted hybridization methodologies remain unchanged except for the inclusion of these agents in the hybridization incubation. As improvements are made in hybridization techniques, they can readily be applied with incorporation of these described reagents.

Typical polynucleotides, as probes or targets, include, but are not limited to, shorter length strands referred to as oligonucleotides. These may be RNA polymers, DNA polymers, mixed hetero-polymers or modifications of them. The length of a polynucleotide target or probe will generally be at least about 15 nucleotides, typically greater than about 30 nucleotides and preferably at least about 50 nucleotides. The upper limit on the number of bases is typically not a critical feature and may reach several kilobases or greater. They may be either natural polymers or synthetic polymers.

Natural oligonucleotides are typically isolated and purified from a natural source by standard fractionation and purification techniques; or may be biologically cloned, amplified and expressed. Synthetic nucleotide polymers may be chemically synthesized using commercially available methods and equipment. For example, the solid phase phosphoramidite method can be used to produce short probes. See, generally, Caruthers, et al., *Cold Spring Harbor Symp. Quant. Biol.,* 47:411–418 (1982); Adams, et al., *J. Am. Chem. Soc.,* 105:661 (1983); and Itakura, et al., *Ann. Rev. Biochem.,* 53:323–356 (1984). DNA may be directly extracted and purified using standard techniques, as may RNA, often additionally using oligo-dT chromatography.

The particular hybridization format employed is not critical, as the invention can be applied, in some embodiment, to all known formats. These formats include both single phase (solution) and mixed phase (solid/solution) assays. The particularities in procedure may depend partly upon the format. As improvements in hybridization formats are made or new formats developed, this invention can be readily applied to them with relatively minor modifications.

In general, hybridization methods comprise a step of combining one or more single stranded target sequences with one or more single strand probes having sufficient base complementarity to anneal under appropriate conditions. Precise sequence complementarity is not generally required, but the specificity of the assays will increase with increased complementarity. Typically, a further step of determining the resulting polynucleotide duplex formed between target and probe will be included. Such assays may include direct detection of duplex formation or perhaps indirect tests by means of a competition assay. Conventional hybridization formats which are particularly useful include those wherein the sample nucleic acid is contained in a cell or cellular structure, including the resulting product of a cellular extraction (in situ), wherein either the polynucleotide target or the polynucleotide probe is immobilized on a solid support (solid-phase hybridization), and those wherein substantially all polynucleotide species are in homogeneous solution (solution hybridization).

The present invention is useful whenever it is desirable to accelerate the rate of hybridization of complementary polynucleotides, at least one of which is in soluble phase. The polymers disclosed also are useful for reducing nonspecific binding of said polynucleotides. This includes RNA, DNA and suitable derivatives of them. The formation of DNA/DNA, RNA/RNA, and RNA/DNA hybrids is accelerated in liquid phase media containing AHPs.

A. In situ Hybridization

In situ hybridization is a method for localizing or detecting target sequences within cells or residual cellular structures using labeled probes. See generally, Singer, et al., supra. This is typically intended to determine the presence or location of the target polynucleotides by hybridization. The localization is within intact cells or subcellular structures or, more typically, within the residual structure after sample preparation corresponding to the natural cellular state. Sample preparation will normally involve fixation or permeabilization of the tissue, cell or subcellular component. Typically, the probes have sufficient sequence complementarity to bind to the target sequences under preselected hybridization conditions.

An in situ hybridization procedure typically comprises a step of fixing cells or tissue sections of the sample to a microscope slide. Typical fixing agents include precipitants, e.g., picric acid and mercuric acid, ethanol, methanol, crosslinking agents, e.g., formaldehyde, glutaraldehyde, paraformaldehyde-lysine/ periodate, ethyldimethylaminopropylcarbodiimide, and dimethyl suberimidate, used at concentrations ranging from about 0.5% to 95%.

This fixation step prevents loss of cells from the slide and often also serves to permeabilize the sample to increase probe diffusion into cells. The polynucleotide probe is usually added at concentrations of at least about 1 $\mu$g/mL to the sample which is heated to a temperature sufficient to denature the double stranded target nucleotide sequence, typically at least about 80° C. The temperature is then lowered to allow for hybridization between the target and probe, typically at about 25° C. This hybridization step is where the AHP of the present invention should be present to accelerate hybridization between target and probe sequences and to lower background binding. The hybridization mixture is incubated, typically at about 25° C. for about 1 hour, or for a sufficient period of time to allow hybridization. After washing to remove unhybridized and nonspecifically bound probe, the hybridized probe is typically detected and localized in accordance with the detectable characteristics of the label.

The present invention is particularly advantageous for in situ hybridization methods since:

1. the acceleration rate is most evident where relatively small amounts of nucleic acid are immobilized and are brought into contact with excess probe in the hybridization medium, and
2. the reduction in background due to nonspecific binding of probe with polynucleotide is particularly dramatic for this hybridization format.

B. Solid-phase Hybridization

In the solid phase hybridization format, one of the polynucleotide species is immobilized on a solid support. These solid supports include those which bind nucleic acids either covalently or non-covalently. Noncovalent supports include such polymers as nitrocellulose, derivatized nylon (i.e. Nytran™ and fluorinated polyhydrocarbons. See Hames and Higgins, infra; T. Maniatis et al. (eds.), *Molecular Cloning; A Laboratory Manual,* Cold Spring Harbor Laboratory (1982). Covalent binding supports typically comprise materials that have reactive moieties on their surfaces that can serve as sites of attachment of an appropriate polynucleotide. Examples of covalent linkages would be diazotized paper, dichlorotriazine diazo-benzyloxy-methoxyl cellulose, agarose activated with cyanogen bromide, Immobilone® (Millipore), or Immunodyne® (Pall Membrane), polystyrene/latex, polystyrene, carboxyl or amine modified latex microspheres, carboxyl or amine modified glass, and carboxyl or amine modified teflon.

Solid phase hybridization assays require the immobilization of a capture nucleic acid to a solid support surface. Methods for the immobilization of nucleic acid to solid supports are known. See, e.g., Bischoff, R. et al., "Introduction of 5'-Terminal Functional Groups into Synthetic Oligonucleotides for Selective Immobilization," *Anal. Biochem.* 164:336-344 (1987); Wolf, S. F. et al., "Rapid Hybridization Kinetics of DNA Attached to Submicron Latex Particles," *Nuc. Acids Res.* 15:2911–2926 (1987); and J. N. Kremsky et al., "Immobilization of DNA via Oligonucleotides Containing an Aldehyde or Carboxylic Acid Group at the 5' Terminus," *Nuc. Acids Res.* 15:2891–2910 (1987).

Methods of linking oligonucleotides to solid supports have been previously described. See, e.g. P. T. Gilham, *J. Am. Chem. Soc.,* 86:4982–4985 (1964); P. T. Gilham, *Biochemistry,* 7:2809–2813 (1968); J.A. Langdale and A. D. B. Malcolm, *Gene,* 36:201–210 (1985); B. C. F. Chu et al., *Nucl. Acids Res.,* 11:6513–6529 (1983); L. Clerici et al., *Nucl. Acids Res.,* 6:247–258 (1979); B. A. Connolly, *Nucl. Acids Res.,* 13:4485–4502 (1985); L. M. Smith et al., *Nucl.*

Acids Res., 13:2399–2412 (1985); R. Bischoff et al., *Anal. Biochem.*, 164:336–344 (1987).

One form of solid phase hybridization is the sandwich assay. In this method, a polynucleotide sequence (capture sequence) complementary to a given sequence on the target polynucleotide species is immobilized on a solid support. The immobolized polynucleotide sequence and a labeled polynucleotide (signal sequence) each complementary to discrete regions on the target polynucleotide are simultaneously hybridized to said target polynucleotide (one step sandwich assay) or, in a two step sandwich assay, the target polynucleotide is first hybridized to the immobilized polynucleotide followed by a second hybridization of the signal sequence to the captured target polynucleotide. In the performance of the sandwich assay, one can use a first set of capture beads to bind the target to a second set of beads, a membrane, a dipstick or a wall of a microtiter well. A typical sandwich assay comprises a step of immobilizing a capture sequence onto the solid support in a single strand form, preferably in the absence of the complementary strand. A sample of the target sequence containing the appropriate labeled sequence and AHP molecules is brought into contact with the immobilized capture sequence under the appropriate conditions of stringency to effect hybridization. The labeled polynucleotide that is bound to the solid support or, alternatively, that is remaining in solution will then be measured after extensive washing in accordance with the detectable characteristic of the label.

A second form of solid phase hybridization is a sequence specific affinity hybridization. A solid phase immobilized sequence may be utilized to select a particular sequence from a solution of polynucleotides, either in a batch procedure, chromatographic column or other similar separation technique.

C. Solution hybridization

In the solution format, both the target and probe nucleic acids are substantially in solution. The target and probe sequences will be denatured, typically by heating to at least about 80° C. in low salt concentrations. The conditions are then changed to allow for the hybridization of complementary strands, typically at lower temperature and higher salt conditions. The AHPs of the present invention will be present at the appropriate concentrations during these hybridization steps.

D. Labels

A virtually unlimited range of labels can be used in hybridization assays benefiting from this invention. Such labels act as reporter groups for detecting duplex formation between a target sequence and its complementary labeled sequence.

A reporter group as used herein is a group which has a physical or chemical characteristic which can be measured or detected. Detection may be achieved by such characteristics as colorimetric, luminescent, or fluorescent labels or by radioactivity; or it may be provided by the ability of the reporter group to serve as a ligand recognition site.

Probes may be labeled by any one of several methods typically used in the art. See, Maniatis et al, *Molecular Cloning: A Laboratory Manual*, Cold Spring Harbor Laboratory (1982). A common method of detection is the use of autoradiography or scintillation detection of $^3H$, $^{125}I$, $^{35}S$, $^{14}C$, or $^{32}P$ labeled probes or the like. The choice of radioisotope depends on research preferences and experimental parameters, including ease of synthesis, stability, half-lives of the isotopes and other factors. Other reporter groups include ligands which are recognized by antibodies or binding molecules labeled with fluorophores, chemiluminescent agents, enzymes or enzyme substrates. Alternatively, probes can be conjugated directly with labels such as fluorophores, chemiluminescent agents, enzymes and enzyme substrates. Alternatively, the same components may be indirectly bonded through a ligand-receptor complex, such as antibodies reactive with a ligand conjugated with label. The choice of label depends on, among other factors, sensitivity required, ease of conjugation with the probe, stability requirements and available instrumentation.

The choice of label dictates the manner in which the label is incorporated into the probe. Radioactive probes are typically made using commercially available nucleotides containing the desired radioactive isotope or by chemical derivatization, modification or incorporation of the isotopic label. Radioactive nucleotides can be incorporated into probes, for example, by using nick-translation, by tailing of radioactive nucleotides to the 3' end of probes with terminal transferase, by copying M13 plasmids having specific inserts with the Klenow fragment of DNA polymerase in the presence of radioactive dNTP's or by transcribing RNA from templates using RNA polymerase in the presence of radioactive dNTP's.

Non-isotopic probes can be labeled directly with a detectable moiety (e.g., fluorophore, chemiluminescent agent, or enzyme) or labeled indirectly by conjugation with a ligand. For example, a ligand molecule may be covalently bound to the probe. This ligand would bind to a receptor molecule which is either inherently detectable or covalently bound to a detectable moiety, such as an enzyme or photoreactive compound. Ligands and receptors may be varied widely. Where a ligand has a natural "receptor molecule" or "anti-ligand", for example, the ligands biotin, thyroxine, and cortisol, it can be used in conjunction with its labeled, naturally occurring receptor. Alternatively, any haptenic or antigenic compound can be used in combination with a suitably labeled antibody.

Enzymes of interest as reporter groups will include hydrolases, particularly phosphatases, esterases, ureases, or glycosidases, or oxidoreductases, particularly peroxidases. Fluorescent compounds include fluorescein and its derivatives, rhodamine and its derivatives, dansyl or coumarins (e.g. 4-methylumbelliferone). Chemiluminescers include, but are not limited to, luciferin, luminol and oxetanediones.

E. Hybridization Conditions

The specific hybridization conditions for which these acceleration polymers may be appropriate are broad and optimization of conditions allow parameters to be varied in accordance with the preferences and needs of the investigators. Various hybridization solutions may be employed, typically comprising from about 20 to 60% volume, preferably about 40%, of a polar organic solvent. A common hybridization solution employs about 30–60% v/v formamide, about 0.05 to 1M sodium chloride, about 0.01 to 0.1M buffers, such as sodium citrate, Tris HCl, PIPES, HEPES or EPPS, about 0.05 to 0.5% detergent, such as sodium dodecylsulfate, and between about 1–10 mM EDTA, about 0.01 to 5% ficoll (about 300–500 kilodaltons), about 0.1 to 5% polyvinylpyrrolidone (about 250–500 kdal) and about 0.01 to 10% bovine serum albumin. Also included in the typical hybridization solution will be unlabeled carrier nucleic acids at about 0.1 to 5 mg/mL, e.g., partially fragmented calf thymus or salmon sperm, DNA, and/or partially fragmented yeast RNA and, optionally, about 0.5 to 2% w/v glycine. Other additives may also be included, such as other "volume exclusion agents" which include dextran sulfate and one or more AHP of the present invention, such as polystyrene sulfonic acid (PSSA).

The particular hybridization format or technique is not critical to the effective use of the invention. Hybridization techniques are generally described in *Nucleic Acid Hybridization, A Practical Approach*, (Hames, B. D. and Higgins, S. J., Eds.) IRL Press, 1985 which is hereby incorporated herein by reference. As improvements are made in hybridization techniques, the present invention can readily be applied to them by inclusion of AHPs during the hybridization incubation.

The amount of labeled probe which is present in the hybridization solution may vary widely. Generally, substantial molar excesses of probe over the amount of the target nucleic acid will be employed to enhance the rate of hybridization of the probe to the target nucleic acid and to increase the signal over background.

Various degrees of stringency of hybridization can be employed. As the conditions for hybridization become more stringent, there must be a greater degree of complementarity between the probe and the target for the formation of a stable duplex. The degree of stringency can be controlled by the temperature, ionic strength, the inclusion of polar organic solvents, and the like. See Wetmur and Davidson, *J. Mol. Biol.*, 31:349 (1968). For example, temperatures employed will normally be in the range of about 20° to about 90° C., usually about 25° to about 75° C. The stringency of hybridization may also be conveniently varied by changing the ionic strength and polarity of the hybridization solution through manipulation of the concentration of salt within the range of about 0.25 to about 1.5 M, and formamide within the range of about 20% to about 50%.

After hybridization at a temperature and time period appropriate for the particular hybridization solution used, the glass, plastic, or filter support to which the probe-target hybrid is attached is introduced into a wash solution typically containing similar reagents as provided in the hybridization solution. These reagents may be at similar concentrations as the hybridization medium, but often they are at modified concentrations when more stringent washing conditions are desired. The time period for which the support is maintained in the wash solutions may vary from minutes to several hours or more.

Either the hybridization or the wash medium or both can be stringent. After appropriate stringent washing, the correct hybridization complex may then be detected in accordance with the nature of the label.

F. Detection

The probe may be conjugated directly with the label. For example, where the label is radioactive, the support surface with associated hybridization complex substrate is typically exposed to X-ray film. Where the label is fluorescent, the sample is typically detected by first irradiating it with light of a particular wavelength. The fluorophore absorbs this light and emits light of a different wavelength which is detected. Where the label is an enzyme, the sample is typically detected by incubation with an appropriate substrate for the enzyme. The signal generated may be a colored precipitate, a colored or fluorescent soluble material or photons generated by bioluminescence or chemiluminescence.

Detection of a hybridization complex may require the binding of a signal generating complex to a duplex of target and probe polynucleotides or nucleic acids. Typically, such binding occurs through ligand and receptor interactions as, for example, between a ligand-conjugated probe and a label conjugated receptor.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to radioactive label.

G. Measurement of hybridization rate

The rate of hybridization on solid supports can be determined by measuring the extent of hybridization at various times and calculating the slope of the line obtained by graphing time vs. extent of hybridization. The rate of hybridization of nucleic acids may be determined in at least two ways. The first involves a series of incubations of different time periods with some determination of time after which no further increase in signal will result.

For homogenous hybridization assays in solution, one can measure the rate of hybridization by the method described and used by Wetmur and Davidson, *J. Mol. Biol.*, 31: 349 (1968).

H. Measurement of non-specific background.

The non-specific background signal may be qualitatively assessed by a method of comparing samples where the specific hybridization is substantially absent. The background signal from non-specific binding will be detectably diminished, as visually determined, in samples where the AHP is included.

It will be evident to one of ordinary skill in the art, in view of the present disclosure, that various similar or equivalent polymers can be used for these purposes without departing from the spirit and scope of the present invention Various substituted vinyl polymers such as polyvinyl sulfonate and polyanethole sulfonate will, under appropriate conditions, have similar hybridization accelerating and background reducing properties as PSSA.

The following experimental section is offered by way of example and not by limitation.

EXPERIMENTAL

GENERAL METHODS

Many of the described methods are modifications of standard methods used in the art. See, e.g., Maniatis et al., *Molecular Coning: A Laboratory Manual*, Cold Spring Harbor Laboratory (1982).

A. Solutions and Buffers

Denhardt's solution is 0.02% Ficoll 400, 0.02% polyvinylpyrrolidone (MW 360,000), 0.02% bovine serum albumin; TN is 100 mM Tris pH 7.5 and 100 mM sodium chloride; TNTG is 100 mM tris pH 7.5, 100 mM sodium chloride, 0.5% Triton X-100, and 1.0% liquid gelatin; TMNZ is 100 mM Tris pH 8.5, 50 mM magnesium chloride, 100 mM sodium chloride, and 0.1 mM zinc chloride; filter wash (FW) is 0.09 M sodium chloride, 50 mM Tris pH 7.6, 25 mM EDTA; SDS/FW is FW and 0.1% SDS; HRP (horseradish peroxidase) substrate solution is 0.1 M sodium citrate pH 5.5, 0.5 mg/ml 4-methoxy-1-naphthol, 0.02 mg/ml 3-methyl-2-benzothiazolinone hydrazone and 0.0135% hydrogen peroxide; AP (alkaline phosphatase) substrate solution is 1 mM 5-bromo-4-chloroidoyl-3-phosphate, 1 mM nitroBlue tetrazolium, and 0.01% Tween 20 in TMNZ; lysis solution is 3M guanidinium thiocyanate, 2% N-lauroylsarcosine (sarcosyl), 50 mM Tris pH 7.6, 25 mM EDTA; the counter stain solution is 0.013% Safranin 0 and 0.1% Orange 2.

B. Cell Culture

CaSki cells (human cervical epidermoid carcinoma), from the American Type Culture Collection (ATCC, CRL1550), were maintained according to the procedures provided by the ATCC. Briefly, the cells were cultured in MEM (minimum essential medium) (Flow Labs) culture medium supplemented with fetal calf serum. Approximately 1×10$^5$ cells in 100 μL of growth medium were inoculated onto glass microscope cover slips and incubated at 37° C. for 12 hours. After this time 2×10$^5$ cells became attached to the cover slips. The cells were fixed in EtOH and the cover slips were glued (cell side up) to a microscope slide using "Super Glue." A negative control cell line, A549 (human lung carcinoma, ATCC CCL185) was maintained for comparison the CaSki cell line.

C. Tissue Collection

Cervical smears or cell samples from the anogenital region, obtained using acceptable medical practices, were immediately fixed in 95% ethanol. Specifically, a cell smear (PAP smear) was placed on a standard microscope slide, sprayed with a 95% ethanol fixative, and stored at −20° C.

D. Probe Preparation 1) Long genomic probes.

Probe DNA's which are complementary to various (HPV) genomes were prepared from recombinant inserts in a pBluescript cloning vector (i.e. pHPV-16 is a genomic sequence of human papilloma virus type 16 inserted into the BamH I restriction site of pBluescript II®). pBluescript II® is a 2.95 kb colony producing phagemid derived by replacing the pUC19 polylinker of pBS (±) with a synthetic polylinker containing 21 unique restriction sites. The probe was labeled with biotin using the protocol of Langer and Waldrop (1981) *Proc. Nat'l Acad. Sci., U.S.A.,* 78:6633–6637. Specifically, the procedure involved the following materials and steps:

Materials:

DNase (ICN Pharmaceuticals) - 4 ug/mL;

DNA Polymerase I (U.S. Biochemical) - 8 U/μL;

pHPV-16-2.16 mg/mL;

10X-DP-1M Tris, pH 7.5 (20 mL), 0.5M DTT (80 μL), 1M MgCl$_2$ (2.8 mL) and H$_2$O (17 mL);

Nucleotide mix-2 mM each dGTP, dCTP, and TTP; and

Bio-11-dUTP, a biotinylated deoxyuridine nucleotide from Sigma Chemicals.

Steps:

To an ice cold mixture of 10X-DP (4 μL), pHPV-16 (2 μL), nucleotide mix (6 μL), and H$_2$O was added DNase (1 μL) and DNA polymerase I (2.4 μL). The reaction mixture was incubated at 16° C. for 1 hour. The DNA was gel purified and the material having a size distribution of 50–150 base pairs was used as probe material at a concentration of 4.2 μ/mL.

2) Oligonucleotides.

Two oligonucleotides complementary to two different regions of the 16S-ribosomal RNA of *Bacteroides gingivalis* were synthesized on an Applied Biosystems DNA synthesizer Model 380B. Sequence A is 5'-GTA TTA CCG CGG CTG CTG-3' and was prepared as the probe oligonucleotide by kinasing the 5' terminus with polynucleotide kinase using procedures described in *Molecular Cloning: A Laboratory Manual*, (T. Maniatis, et al. eds.) Cold Spring Harbor Laboratory, p. 148, (1982). Sequence B is 5'- X-CTG CTG CCT CCC GTA GGA GT-3' where X is an amino hexyl phosphate on the 5' terminus. Sequence B was used as the capture oligonucleotide in a sandwich hybridization assay.

EXAMPLE 1

In Situ Hybridization

E. The Use of a Size Exclusion Agent in an In Situ Hybridization in CaSki Cells and Cervical Smears CaSki cells or cervical smears, fixed on a microscope slide as previously described, were covered with hybridization solution (5 μL/cm$^2$) containing 4.2 μg/mL biotinylated probe, 40% formamide, 12% polystyrene sulfonic acid (PSSA; 125,000 dalton, pH 7.5), 20 mM EPPS buffer, 200 μg/mL salmon sperm DNA (base hydrolysed), 200 μg/mL partially hydrolysed yeast tRNA, 0.05% w/v sodium pyrophosphate, 5 mM EDTA, 1×Denhardt's reagent, 100 mM sodium chloride and 0.05% w/v SDS. The slides were loosely wrapped in Saran® plastic wrap leaving approximately 1 mm between slides. Air bubbles were carefully removed and the slides are placed in a plastic box and floated in a 90° C. water bath for 12 minutes to denature the target nucleic acids. The box was removed from the water bath and incubated at 25° C. for 1 hour to allow hybridization. The Saran wrap was carefully removed and the slides washed at stringent conditions with 40% formamide, 50 mM Tris pH 7.5, and 50 mM sodium chloride for 10 minutes at room temperature. The slides were then washed once in TN for 5 minutes at room temperature and then three times in TNTG for 10 minutes/wash at room temperature. They were placed in a Coplin jar and incubated for 30 minutes in a TNTG solution of streptavidin/alkaline phosphatase conjugate (2 μg/mL) at room temperature. After being washed three times in TMNZ for 5 minutes/wash at room temperature, the slides were then incubated in AP substrate solution for about 60 minutes at 37° C. The slides were washed once in water for one minute and then stained with counter stain solution using the following protocol:

a) One minute in counter stain solution
b) Water washes until the water is colorless
c) Air dry at room temperature
d) Dip into xylene and mount immediately The slides were then viewed under a microscope. The slides were judged according to intactness of morphology, presence or absence of background, and presence or absence of nuclear staining. Slides positive for HPV sequences will show a distinct staining of the nucleus with minimal staining of cytoplasmic regions (background) and a majority of the cells having good morphology. A negative slide would have no nuclear staining, minimal background, and good morphology. An indeterminant slide would have either poor morphology, substantial background, or both.

The use of a size exclusion agent was essential in order to detect any hybridization of signal probe to target. PSSA and dextran sulfate were comparable in their ability to enhance the rate and extent of hybridization as determined by the presence of nuclear staining in positive samples. In the absence of a size exclusion agent or in the presence of polyethylene glycol or polyacrylates no detectable staining is observed. Additionally, PSSA significantly reduced probe related background staining. In comparable trials using polyacrylates, polyethylene glycols or dextran sulfate, no reduction in background was observed.

EXAMPLE 2

Sandwich Assay

F. The Use of a Size Exclusion Agent in the Detection of Bacteroids Gingivalis Specific Nucleotide Sequences in a Sandwich Assay Format Preparation of Iodoacetamidobenzoylated Oligonucleotides 10 to 1000 μg of 5'-terminal amine-linked oligonucleotide (Sequence B) were reacted with an excess of N-succinimidyl 4-(iodoacetamido)-benzoate (SIAB) in an alkaline (pH 8.0 preferably) buffer at 18 to 25° C. for 30 to 120 minutes. The unreacted SIAB was removed by size exclusion chromatography on a NAP 25 (Pharmacia) column.

Preparation of the Solid Support

A 16 cm² piece of Nytran® (a charge-modified nylon-66 solid support medium made by Schleicher & Schuell) was incubated for 30 minutes at ambient temperature with 10 ml of 5 mg/ml iminothiolane in 0.1M sodium borate at pH 8.3. The membrane was washed with 5 changes of the sodium borate buffer described above and the presence and quantification of introduced sulfhydryl groups was determined using 5,5-dithio-bis (2-nitrobenzoic acid). The derived membrane was then cut into 0.28 cm² discs and washed once with 0.1M sodium borate buffer.

IAB-oligonucleotide was prepared as described above and mixed with the membrane discs. 300 membrane discs were submerged in 2 ml of 0.1M sodium borate buffer containing 1.0 mg of IAB-oligonucleotide (Sequence B) and the reaction was allowed to proceed at room temperature with constant agitation for 16 hours in the dark.

The discs were then washed sequentially with 0.1M sodium borate, SDS/FW. 1.2 µg of sequence B oligonucleotide were bound per filter disc. The unreacted sulfhydryl groups were then capped with 50 mg/ml iodoacetamide in 0.1M sodium borate pH 8.3. The filters were then washed further with sodium borate and SDS/FW.

Lysis of Bacteria and Hybridization to rRNA $1\times10^8$ cells of Bacteroides gingivalis (Bg) were lysed in 100 µL of 2× lysis solution at 19° C. The cell lysate was then heated in a 65° C. water bath for 10 minutes. The solution was then adjusted to either 0%, 5%, 10% or 15% PSSA or dextran sulfate (DS) in a final volume of 200 µL (1× lysis solution). Radiolabeled probe (Sequence A) ($1\times10^6$ cpm at a specific activity of $1\times10^7$ cpm per microgram) complementary to conserved. regions of bacterial 16S rRNA was added to the lysate solutions to a final concentration of 100 ng/mL. The solutions were incubated with Nytran™ discs which had been covalently immobilized with 0.5 µg of Sequence B oligonucleotide probe (capture probe) for the indicated times at ambient temperature with mild agitation. The solid supports were then washed 3 times with the respective hybridization (1× lysis solution containing the appropriate amount of exclusion agent) solution followed by a wash in SDS/FW at ambient temperature and then counted in a scintillation counter. Triplicate reactions were determined for each time point. See Table 1 below.

TABLE 1

EXTENT OF HYBRIDIZATON vs. TIME
solution hybridization

| TIME | CPM (average of 3 experiments) | | | | |
|---|---|---|---|---|---|
| | 0% PSSA | 5% PSSA | 10% PSSA | 15% PSSA | 10% DS |
| 0 | 0 | 0 | 0 | 0 | 0 |
| 20 | 1991 | 2415 | 2582 | 1877 | 1615 |
| 40 | 2504 | 3241 | 3526 | 2559 | 2623 |
| 60 | 3103 | 4804 | 4509 | 3200 | 3339 |

TABLE 1-continued

SOLID PHASE HYBRIDIZATION

| Concentration of Volume Exclusion Agent | Relative Extent | Relative Rate |
|---|---|---|
| 0% PSSA | 1x | 1x |
| 5% PSSA | 1.3x | 1.7x |
| 10% PSSA | 1.4x | 1.7x |
| 15% PSSA | 1.0x | 1.0x |
| 10% Dextran Sulfate | 1.0x | 1.0x |

Each and every reference cited herein, both academic articles and patent references, is incorporated into the disclosure by reference.

Although the present invention has been described in some detail by way of illustration and example for the purposes of clarity of understanding, it will be apparent that certain changes and modifications may be practiced within the scope of claims.

What is claimed is:

1. A method for conducting a nucleic acid hybridization assay in a hybridization medium containing complementary nucleic acid sequences, comprising:

adding polystyrene sulfonic acid to the hybridization medium in an amount to lower non-specific hybridization by at least 15%; and detecting the presence of hybridized nucleic acid.

2. A method as in claim 1, wherein the polystyrene sulfonic acid has a molecular weight of 10,000 daltons to 500,000 daltons.

3. A method as in claim 1, wherein the nucleic acid hybridization is in situ hybridization and the polystyrene sulfonic acid is at a concentration of about 12%.

4. A method as in claim 1, wherein the nucleic acid hybridization is a solid phase hybridization and the polystyrene sulfonic acid is at a concentration of about 5%.

5. A method for improved hybridization assays of complementary polynucleotides comprising contacting a target polynucleotide and a complementary polynucleotide in a hybridization medium, which hybridization medium contains polystyrene sulfonic acid in an amount sufficient to lower non-specific hybridization by at least 15%.

6. A method as in claim 5, wherein the polystyrene sulfonic acid has a molecular weight of 10,000 daltons to 500,000 daltons.

7. A method as in claim 5, wherein the hybridization assay is an in situ assay and the polystyrene sulfonic acid is at a concentration of about 12%.

8. A method as in claim 5, wherein the hybridization assay is a solid phase assay and the polystyrene sulfonic acid is at a concentration of about 5%.

* * * * *

UNITED STATES PATENT AND TRADEMARK OFFICE
CERTIFICATE OF CORRECTION

PATENT NO. : 5,853,986
DATED : December 29, 1998
INVENTOR(S) : Charles Robert Petrie, III, et al.

It is certified that error appears in the above-identified patent and that said Letters Patent is hereby corrected as shown below:

On the title page item [45], insert an asterisk [*], before the patent date.

On the title page following the assignee data, insert:

--[Notice]: Under 35 U.S.C. 154, the term of this patent shall be extended for 262 days.--

Signed and Sealed this

Fourth Day of May, 1999

*Attest:*

*Attesting Officer*

Q. TODD DICKINSON

*Acting Commissioner of Patents and Trademarks*